United States Patent
Rollins

(10) Patent No.: US 9,844,692 B2
(45) Date of Patent: Dec. 19, 2017

(54) COMPACT SMART PHONE ENABLED SYSTEM FOR STRENGTH AND ENDURANCE TRAINING

(71) Applicant: Joseph Gregory Rollins, Henderson, NV (US)

(72) Inventor: Joseph Gregory Rollins, Henderson, NV (US)

(*) Notice: Subject to any disclaimer, the term of this patent is extended or adjusted under 35 U.S.C. 154(b) by 57 days.

(21) Appl. No.: 15/136,901

(22) Filed: Apr. 23, 2016

(65) Prior Publication Data
US 2016/0332019 A1 Nov. 17, 2016

Related U.S. Application Data

(60) Provisional application No. 62/161,883, filed on May 15, 2015.

(51) Int. Cl.
*A63B 24/00* (2006.01)
*A63B 21/005* (2006.01)
(Continued)

(52) U.S. Cl.
CPC ...... *A63B 21/0058* (2013.01); *A63B 21/0442* (2013.01); *A63B 21/153* (2013.01); *A63B 21/4034* (2015.10); *A63B 21/4035* (2015.10); *A63B 23/0355* (2013.01); *A63B 23/03508* (2013.01); *A63B 23/03541* (2013.01); *A63B 23/129* (2013.01); *A63B 23/1218* (2013.01); *A63B 23/1254* (2013.01);
(Continued)

(58) Field of Classification Search
CPC .............. A63B 21/0058; A63B 21/153; A63B 21/4035; A63B 21/4034; A63B 21/0442; A63B 21/1645; A63B 21/1654; A63B 24/0062; A63B 24/0075; A63B 24/0087; A63B 23/03508; A63B 23/03541; A63B 23/0355; A63B 23/1218; A63B 23/1254; A63B 23/129; A63B 2209/10; G06F 19/3481
See application file for complete search history.

(56) References Cited

U.S. PATENT DOCUMENTS 6,280,361 B1 * 8/2001 Harvey ............... A63B 21/025
482/101
2009/0247375 A1 * 10/2009 Smith ............... A63B 21/0004
482/110
(Continued)

*Primary Examiner* — Glenn Richman

(57) ABSTRACT

This invention is a portable exercise system capable of performing multiple exercises for strength and endurance training. The key component is the force generation unit (FGU) which is small and light enough to be suspended during the exercise yet capable of producing a force of 50 lbs. The FGU is programmable allowing it to generate various force vs distance, time or velocity profiles. Different handles, cables and attachments can be connected or used with the FGU perform different exercises. The FGU can charge its battery from the user's energy during use. The FGU can communicate bidirectionally with computers and smart phones for setup and to track the user's performance. Multiple FGUs may be used simultaneously each performing a separate function. The entire system is small enough to fit in a drawer or suitcase. The accompanying software can track the user's performance and function as an automated personal trainer.

15 Claims, 9 Drawing Sheets

(51) Int. Cl.
    *A63B 21/00*     (2006.01)
    *A63B 21/04*     (2006.01)
    *A63B 23/035*     (2006.01)
    *A63B 23/12*     (2006.01)
    *G06F 19/00*     (2011.01)
    *H02J 7/00*     (2006.01)
    *A63B 21/16*     (2006.01)

(52) U.S. Cl.
    CPC ...... *A63B 24/0062* (2013.01); *A63B 24/0075* (2013.01); *A63B 24/0087* (2013.01); *G06F 19/3481* (2013.01); *H02J 7/00* (2013.01); *A63B 21/154* (2013.01); *A63B 21/1645* (2013.01); *A63B 21/1654* (2013.01); *A63B 2209/10* (2013.01)

(56) References Cited

U.S. PATENT DOCUMENTS

2013/0310230 A1*  11/2013  Norris .................. A63B 21/018
                                                                                             482/115
2014/0287876 A1*   9/2014  Etter .................. A63B 24/0087
                                                                                             482/5
2015/0306459 A1*  10/2015  Boyette ............. A63B 24/0075
                                                                                             482/5

* cited by examiner

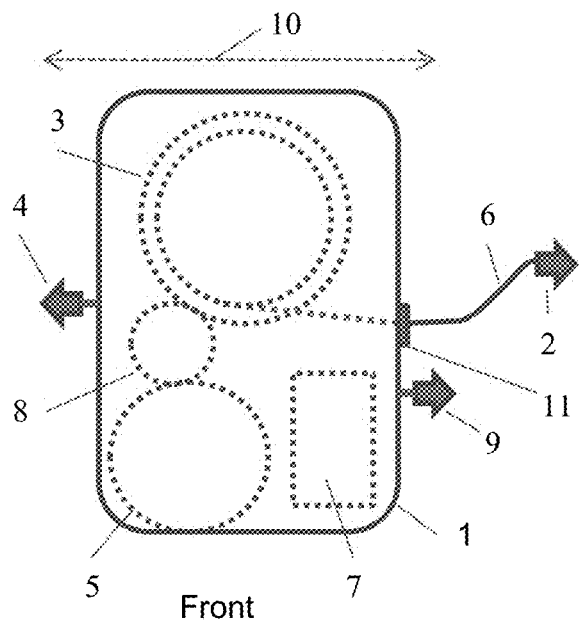
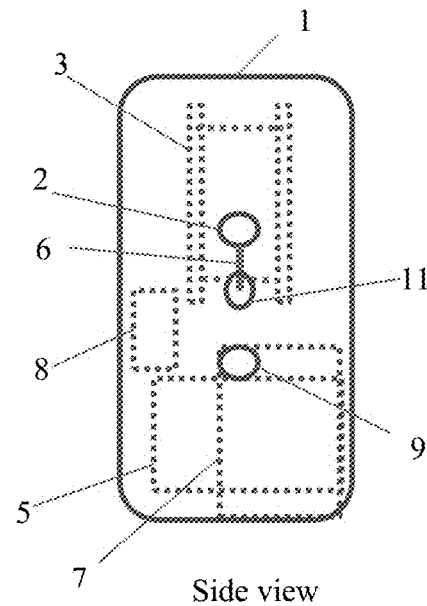
FIG. 1A        FIG. 1B
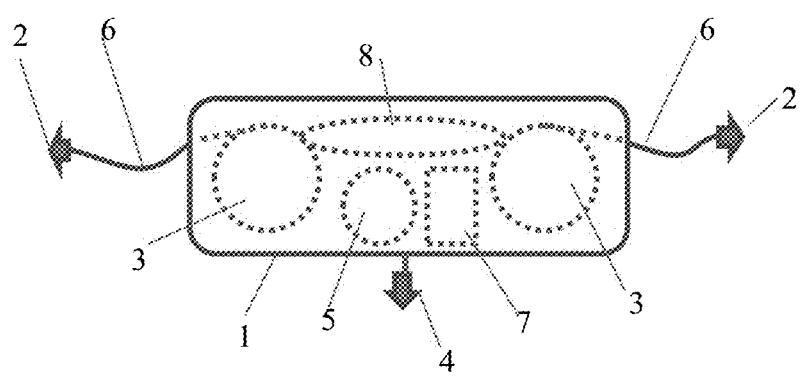
FIG. 2

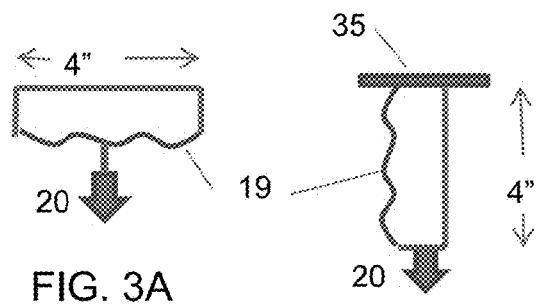
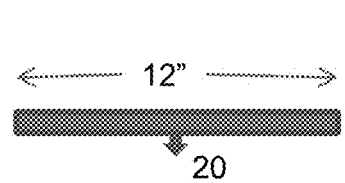
FIG. 3A
FIG. 3B
FIG. 3C
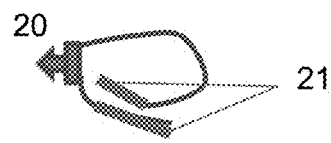
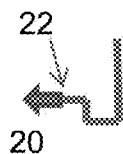
FIG. 3D
FIG. 3E
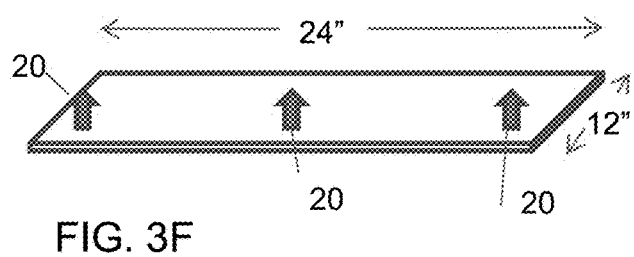
FIG. 3F
FIG. 3G
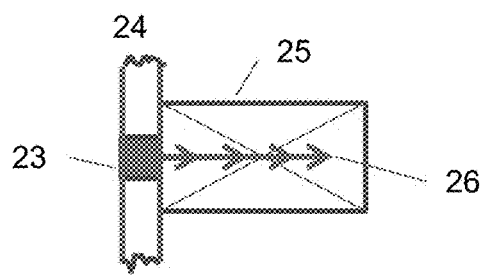
FIG. 3H

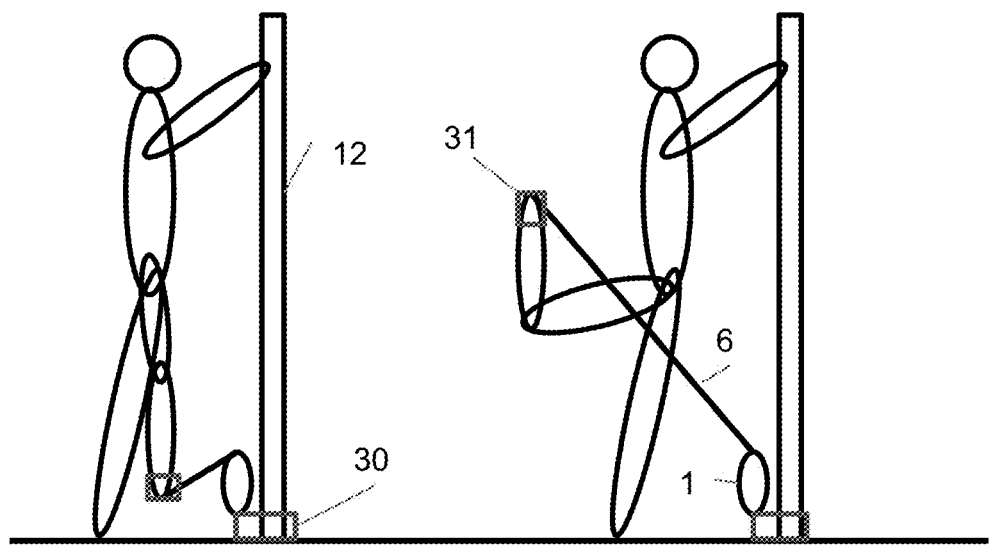
FIG. 7
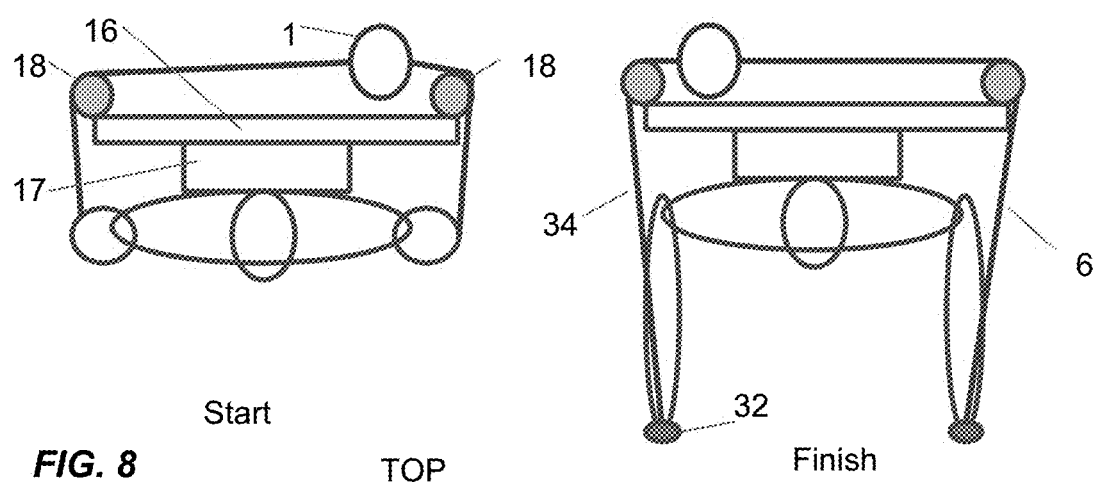
FIG. 8  Start  TOP  Finish

COMPACT SMART PHONE ENABLED SYSTEM FOR STRENGTH AND ENDURANCE TRAINING

CROSS REFERENCE TO RELATED APPLICATIONS

Provisional Patent: "Compact smart-phone enabled exercise system for strength and endurance training", Joseph Gregory Rollins, Application ID 62161883, 15 May 2015

BACKGROUND OF THE INVENTION

This invention is a portable exercise system capable of performing multiple exercises for strength and endurance training. To allow ease of use the exerciser may be controlled by a smart phone or computer.

An electrically operated exercise machine has important advantages over a purely mechanical machine of ease of setup, precise control and detailed monitoring of performance.

Recent advances in technology have allowed the development of very small, yet powerful motors. For example, a motor less than 3 inches long and 2 inches in diameter can produce ⅓ horse-power for intervals of several minutes. Likewise, "C" sized batteries can produce currents of 50 A for several minutes. This invention takes advantage of these advances to produce a machine which is compact, powerful and versatile.

BRIEF SUMMARY OF THE INVENTION

This invention is a portable exercise system capable of performing multiple exercises for strength and endurance training. The key component is the force generation unit (FGU) which is small and light enough to be suspended during the exercise yet capable of producing a force of 50 lbs. The FGU is programmable allowing it to generate various force vs distance, time or velocity profiles. Different handles, cables and attachments can be connected or used with the FGU perform different exercises. The FGU can charge its battery from the user's energy during use. The FGU can communicate bidirectionally with computers and smart phones for setup and to track the user's performance. Multiple FGUs may be used simultaneously each performing a separate function. The entire system is small enough to fit in a drawer or suitcase. The accompanying software can track the user's performance and function as an automated personal trainer.

BRIEF DESCRIPTION OF THE SEVERAL VIEWS OF THE DRAWING

FIG. 1A Force generation unit (FGU). housing 1, moving quick release connector (QRC) 2, spool 3, main fixed QRC 4, drive motor 5, retractable cable 6, battery and electronics 7, gearing 8, alternate fixed QRC 9, minimum dimension with cable fully retracted 10, cable entry bushing 11, FIG. 1B Side view of FGU FIG. 2 Alternate FGU configuration with 2 spools and 2 moving connectors FIG. 3A Short handle detachable accessory. QRC 20, rubber covering 19.

FIG. 3B Short grip detachable accessory. QRC 20, rubber covering 19,

FIG. 3C Medium handle detachable accessory. QRC 20

FIG. 3D Foot loop detachable accessory. QRC 20, Velcro pads 21.

FIG. 3E Door attach detachable accessory. QRC 20, pivot joint 22.

FIG. 3F Floor plate accessory. QRC 20.

FIG. 3G Extension cable accessory. QRC 20.

FIG. 3H Wall attachment accessory. Screw head containing QRC 23, dry-wall, subfloor or door casing 24, stud, joist or door header 25, wood screw 26.

FIG. 7 Leg exercise. FGU 1, FGU cable 6, door 12, door attachment placed under bottom edge of door 30, foot loop 31 placed around ankle.

FIG. 8 Chest Exercise with pulley bar attachment. Cylindrical bar 16, approx. 1" in dia and 24" long with a pulley 18, at each end and resilient pad 17, in the center, extension cable 34, short handle 32, FGU 1, FGU cable 6. Note the FGU is pulled along the length of the bar 16, by the extension cable 34.

DETAILED DESCRIPTION OF THE INVENTION

Figure 3I:
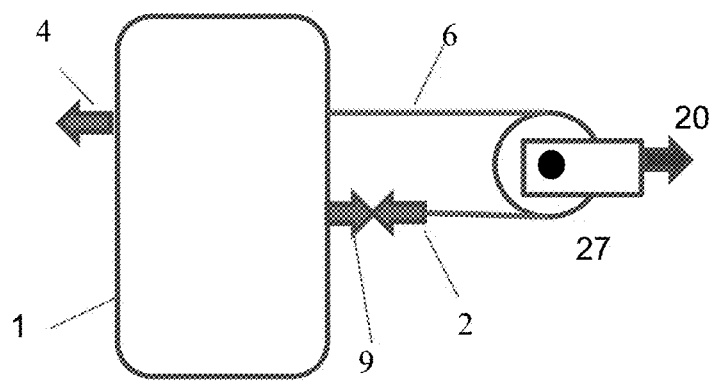
FIG. 3I Force doubling pulley attachment. Small pulley 27, QRC 20

The key system component, the FGU (See FIG. 1) contains an electric motor 5, cable 6, spool 3, transmission 8, rechargeable battery and electronics system 7. The motor, through the transmission 8 (gears or pulleys and belts) turns the spool to retract the flexible cable. The cable 6 should have a fully extended length of 8 feet or more. Quick release connectors (QRC) 4 and 9 are attached to the body of the FGU and to the end of the cable 2. These connectors are for a mechanical connection only, they do not perform any electrical connection. Exercise accessories are attached to the FGU by these connectors. The FGU should be approximately 3"×3"×6" in size and weigh 2 lbs or less. For many exercises the FGU will be suspended in the air by its cable(s) so keeping its weight low is important. It is desirable to keep dimension 10 in FIG. 1 (the minimum distance between the fixed and movable connector) as small as possible. Dimension 10 determines the minimum distance between the two handles (or one handle and a fixed mounting point) and for many exercises the two need to be close together. The cable emerges from the center of the FGU through hole 11 straight off the spool without any bends. Fixed QRC 4 is mounted on the opposite side of the FGU from where the cable emerges so the cable will remain straight when under tension. Hole 11 could be replaced with a slot perpendicular to the spool axis, to allow the cable to be pulled from several angles. The FGU should be capable of generating a force of 50 lbs or greater, and retracting its cable under light load at 2 fps or greater.

Figure 11:
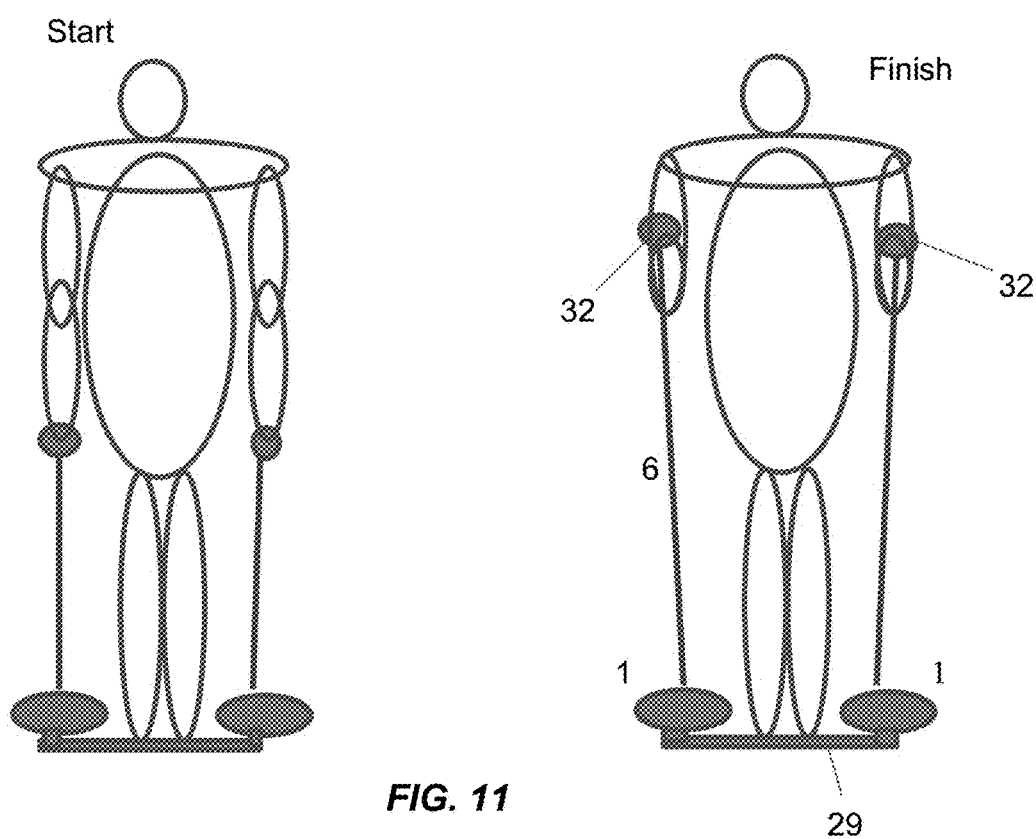
FIG. 11 Biceps curl using 2 FGU units. Two FGU 1, one for each arm, FGU cable 6, floor plate 29, short handle 32.

Multiple FGUs can be used simultaneously (in parallel) to increase the required force or power or perform more complicated exercises (See FIG. 11). For example, use one FGU for each arm, in this case both FGUs would execute the same "program" so the weight for each arm would be the same. However, this need not always be the case, one FGU could be used for an arm and another for a leg in which case they would execute different programs. In this mode the FGUs could communicate with each other or both to an external computer/smart-phone to ensure synchronization.

Different sizes or types of FGU and accessory sets can be offered. An FGU with two opposed cables (see FIG. 2) may be useful. For strength training a larger force may be desired, for endurance training a larger cable retraction velocity. The tradeoff between the two (for a given motor/battery) is determined by the gear ratio, and FGUs with different gear ratios could be offered (or else the FGU could have gear selector and offer selection of several ratios).

Attachment Accessories

FIGS. 3A-3I show a set of attachments to the FGU. Table 1 illustrates their use. More attachments are possible. Each attachment has a QRC (indicated by heavy arrow) which mates to a QRC on the FGU or with the QRC of another attachment.

FIG. 3A, is the short handle. A short rigid cylinder, approx. 4 inches long, and 1 inch diameter. It has a soft covering 19 and is used with one hand. The QRC 20 passes between the middle and ring fingers. The cable pulls perpendicular to the cylinder axis.

FIG. 3B, is the short grip. A short rigid cylinder, approx. 4 inches long and 1 inch diameter. It has a soft covering 19 and is used with one hand. The QRC 20 is at one end and there is a disk 35 approx. 2" dia at the opposite end to stop the grip from sliding through the hand. The cable pulls parallel to the cylinder axis.

FIG. 3C is the medium handle, A thin rigid cylinder, approximately 12" long and 1" in diameter. It is gripped with both hands. The QRC is at its midpoint. The cable pulls perpendicular to the cylinder axis.

FIG. 3D is the foot or leg loop. It is a strap of heavy cloth, approx. 2" wide with a QRC 20 and a Velcro closure 21. It wraps around the leg, ankle or foot. The cable pulls perpendicular to the leg or ankle.

FIG. 3E is the temporary door attachment. It "U" shaped and made of thin stiff metal with an elastic non-scratch covering. A QRC 20, is attached to one end with a pivoting joint 22. It is placed around the side, top or bottom of the door. The door is then closed holding it into place. When the cable is attached it pulls approximately perpendicular to the surface of the door.

FIG. 3F is the floor plate, approx. 12" wide and 24" long made out of thin stiff light weight material and fitted with three QRCs 20. If one FGU is used the user attaches it to the center QRC and stands on the plate with one foot on each side of the center QRC. If two FGUs are used, the user attaches one to each of the two outside QRs and stands in the center of the plate.

FIG. 3G is the extension cable. A thin flexible cable approximately 18 inches long with a QRC 20 at each end.

FIG. 3H is the semi-permanent wall attachment. It is a large wood screw, approx. 3" long and ¼" in diameter. The head of this screw 23, contains a QRC and is approx. ½" in diameter. It screws through the drywall 24, (in a pre-drilled hole) and into a stud 25. It is tightened until the head 23 is flush with the surface of the drywall 24. It forms a strong but unobtrusive fixed point attachment for the exerciser. It can be used in a similar way through carpet and the wood sub-floor into a floor joist or through the top casement of a door into the header, to form ground level and overhead attachment points.

FIG. 3I, is the force doubling pulley. It consists of a small pulley with a QRC attached. It will double the generated force at the expense of retraction speed.

The following table describes some of the exercises that may be performed and which attachments are used.

TABLE 1

Some possible exercises and their configuration.

| Exercise Name | Moving Attachment | Fixed Attachment | FIG. |
| --- | --- | --- | --- |
| Wrist extension or curl | 3A | 3D or 3F | |
| Bicep curl | 3A or 3B | 3D or 3F | 11 |
| Tricep extension | 3A or 3B | 3H or 3E | |
| Tricep & deltoid | 2X (3A or 3B) | none | 9 |
| Quad extension, hip flexor | 3D | 3D + chair or shoulder strap | 10 |
| Hamstring curl | 3D | 3E or 3H | |
| Rowing | 3C | 3E or 3H + rowing kit | 6 |
| Deadlift, Compound lift | 3C | 3F or 3F with 3I | 5 |
| Chest press | 2X (3A or 3B) | Pulley bar | 8 |
| Gluteus & calf | 3D | 3H or 3E | 7 |
| Wood chop (up or down) | SH or SG | 3H or 3E | |
| Latissimus pull down | 3C | 3H to top door frame | |
| Punching | 2X FGU and 2X 3A | 3H or 3E | |
| Front or side kick | 3D | 3H or 3E | |

Attachments: 3A=short handle, 3B=short grip. 3D=foot loop, 3F=floor plate, 3E=door anchor, 3C=medium handle, 3I=force doubling pulley, 3H=wall attachment, see corresponding figures.

Power Management Features

The compact battery used can only power the motor at full output for about 15 minutes. Therefor it is desirable for the FGU shut down quickly once an exercise is completed to charge its battery during use. During most exercises the user is expending energy which can be captured by the FGU to recharge its internal battery. A power dissipation circuit may be needed to prevent overcharging the battery.

During exercise the user is always pulling against the motor. If the user applies enough force to the FGU to overcome the motor force, the cable is pulled out of the FGU. In this case the motor becomes a generator and its generated EMF adds to that of the battery so less battery voltage is needed to maintain a constant force. If the user is pulling fast enough, the generated EMF will become larger than the battery voltage Vbatt and the EMF can be used to charge the battery. However, the battery connection to the motor must be reversed to do this. The velocity at which power become available to charge the battery is $$V = \pi * D/G * Kv * (Vbatt + I * Rm) \quad (5)$$

Here D is the spool diameter, G is the gearing constant, Kv is the motor voltage constant, I is the motor current and Rm is the motor resistance.

As the user releases his pull against the FGU, the cable will be retracted back into the FGU by the motor. The motors generated EMF is effectively subtracted from the battery voltage, so more applied voltage is needed to maintain a constant force. At the maximum retraction velocity, the battery voltage equals the motor EMF so the maximum retraction velocity is also given by Eqn 5. There is a tradeoff on Vbatt. If Vbatt is too small FGU will retract too slowly, if Vbatt is too high it will be difficult for the user to pull fast enough to recharge the battery.

Figure 4:
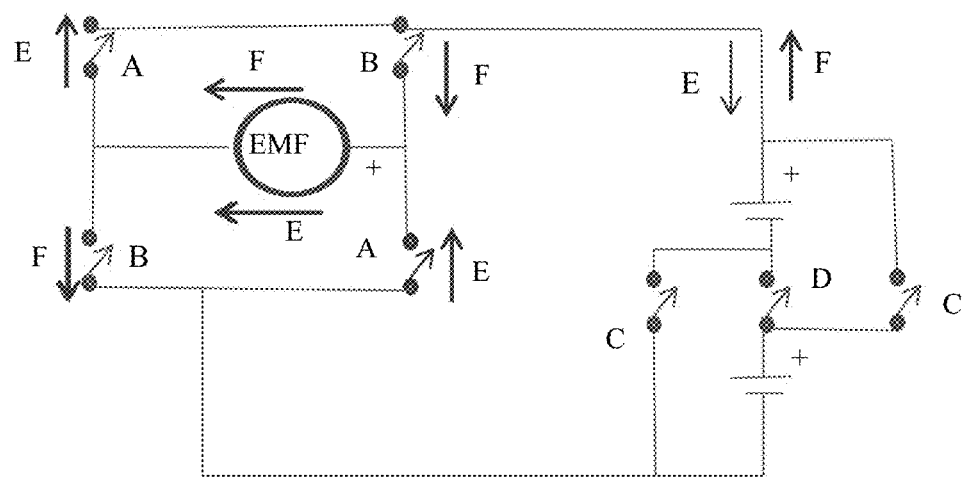
FIG. 4 Power flow diagram. A,B,C,D are MOSFET switches, Arrows E indicate current direction with motor as generator charging battery, Arrows F indicate current direction with motor as a motor draining battery.

If a multiple cell battery is used, the cells can be placed in series, (giving maximum Vbatt) during cable retraction to maximize retraction speed, and in parallel (minimum Vbatt) during cable extension to reduce the extension speed required to charge the battery. FIG. 4 shows circuitry capable of reversing the battery connection (for charging) and changing the battery connection from series to parallel. Table 2 below shows which switches are ON during each operation. The "E" arrows indicate the current flow direction when the motor is working as a "motor" and the "F" arrows the current flow when the motor is working as a generator. All switches are electronic (MOSFETS or BJTs). Note that due to the rapidity of the movement, the controlling electronics must be able to determine and apply the required operational condition in a time interval of less than 100 mS.

TABLE 2

Battery control switch operation

| Cable direction | Speed | Battery | Motor | ON Switches |
|---|---|---|---|---|
| Extend | Fast | High V | Charging | A D |
| Extend | Med | Low V | Charging | A C |
| Extend | Slow | Low V | Breaking | B C |
| Retract | Slow | Low V | Running | B C |
| Retract | Fast | High V | Running | B D |

Exercise Decomposition into Movements

Some exercises may require more than a simple constant force. These exercises may be constructed from multiple "movements" which are executed consecutively. A movement is described by a direction, a starting position Xs, starting force Fs, ending position Xe, and ending force Fe. Between the start and end points linear interpolation is used to calculate the applied force:

$F(x)=Fs+(Fe-Fs)*(X-Xs)/(Xe-Xs)$

Existing strength training machines use a fixed weight with cam shaped pulleys and cables to create such a force profile.

Typically, the starting point Xs of one movement will begin before the ending point of the previous movement, so that is there is overlap between consecutive movements. If the cable position is in this overlap region and the FGU detects a pause in motion, then the FGU switches to the next movement. Other ways of detecting the time to switch to the next movement might be a voice command, or pushing a switch with finger or foot.

For each exercise, the cable starts fully retracted X=0 and the motor is OFF. The user then attaches the appropriate handles to the quick release connectors and pulls the cable to a position greater than Xs for the first movement. During the preceding step the FGU detects the cable movement, turns ON the motor and applies only enough force to prevent the cable from tangling. Once the cable reaches the starting position for the first movement and the user pauses, the FGU applies the starting force for the first movement. Likewise, after the last movement is completed, the cable is retracted with only enough force to prevent the cable from tangling back to X=0 and the motor is turned OFF.

Figure 5:
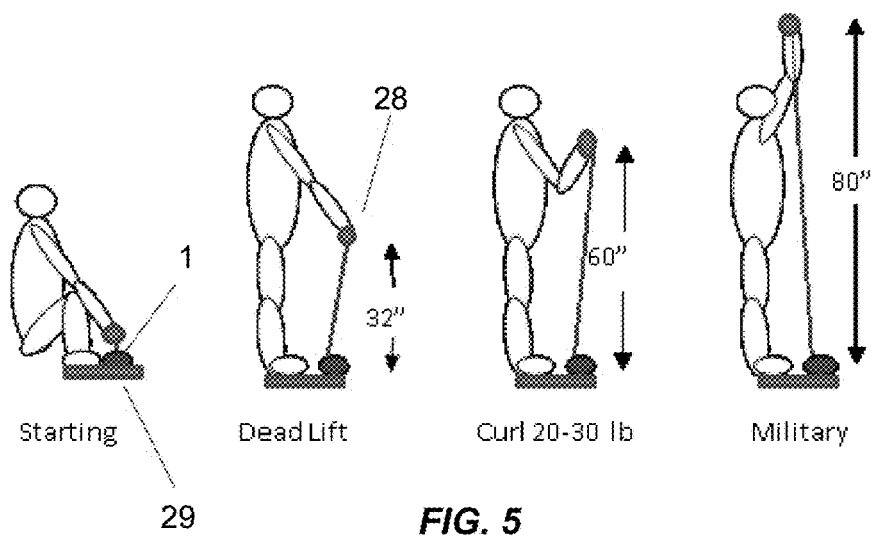
FIG. 5. Exercise with 3 movements. FGU 1, attached to floor plate 29. User is standing on floor plate 29, holding Medium handle 28 with both hands.
Figure 6:
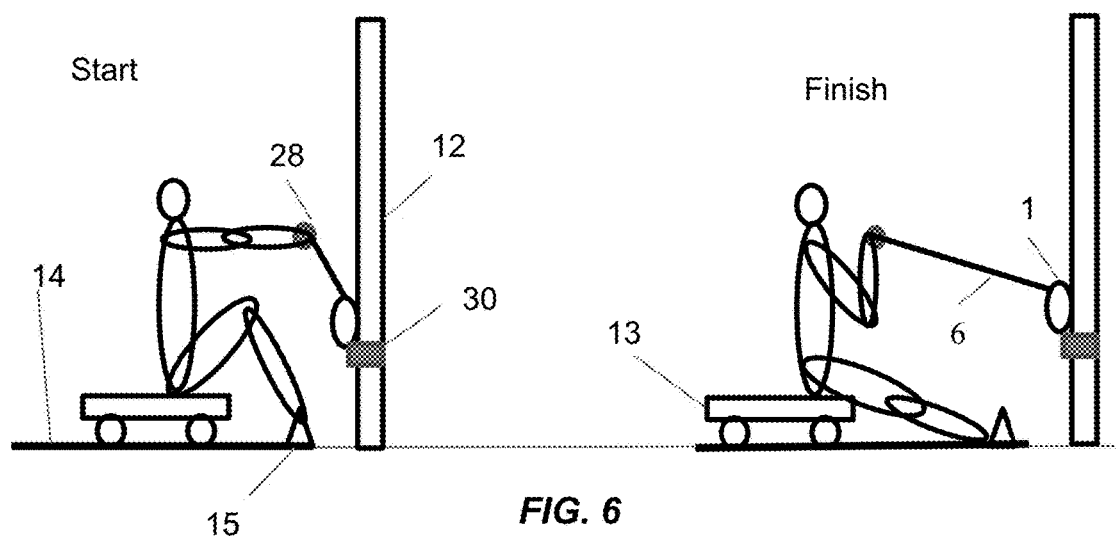
FIG. 6 Rowing exercise, door 12, sliding seat of rowing accessory 13, base of rowing accessory with tracks 15, foot rest attached to base of rowing accessory 15, door attachment placed around side edge of door 30, FGU 1, FGU cable 6, medium handle 28 held with both hands.
Figure 9:
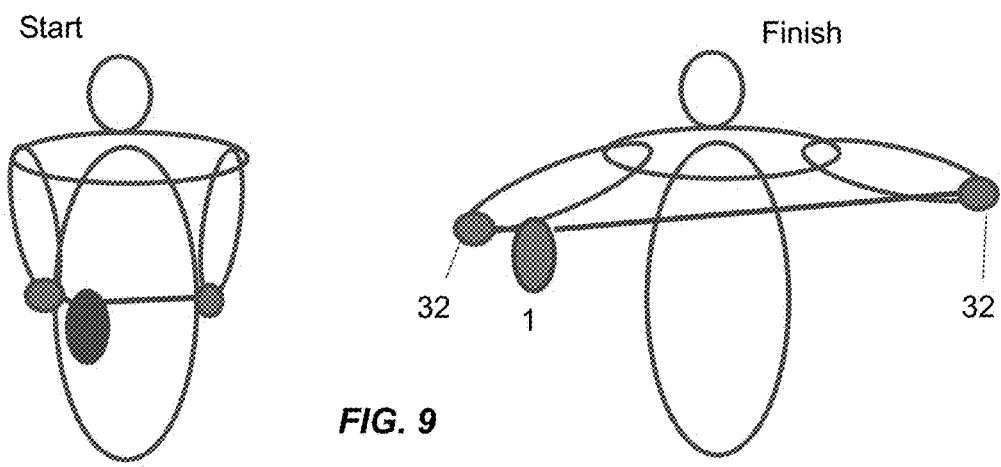
FIG. 9 Shoulder exercise. Two short handles 32, one gripped in each hand.
Figure 10:
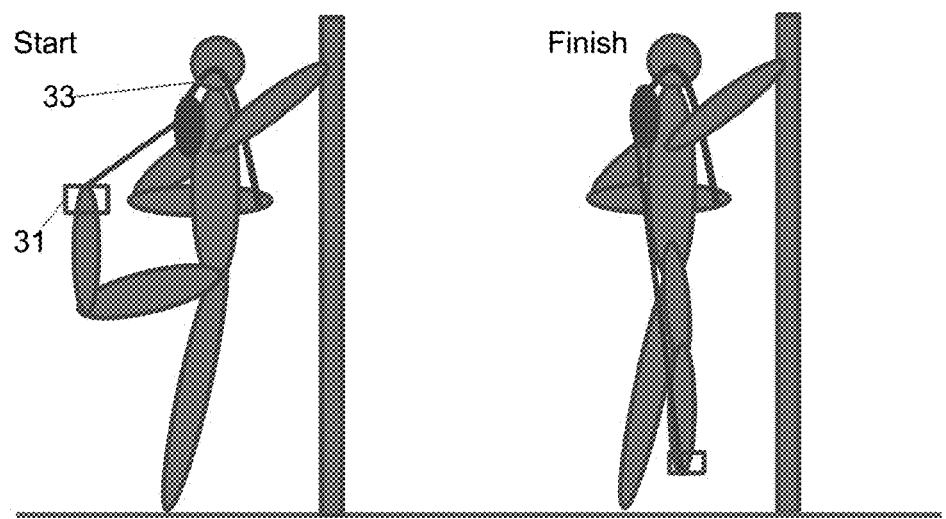
FIG. 10 Leg extension exercise. Shoulder strap 33, a cloth strap approx. 2" wide and 24" long with QRC at one end, is placed over shoulder and attached to FGU with the QRC, a foot loop 31 is placed on foot and attached to FGU cable.

FIG. 5 and Table 3 below show a "compound exercise" consisting of a deadlift, curl and military press. For the deadlift the weight is to be a constant 50 lbs, for the curl the weight should start at 20 lbs and increase to 30 lbs. and for the military press the weight should be a constant 40 lbs. The following table shows the values for each movement. The weight values would be selected by the user, but the distance values (Xs and Xe) would be calculated by the software from the user's height.

TABLE 3

Position and forces for a compound exercise

| Movement | Direction | Xs | Xe | Fs | Fe |
|---|---|---|---|---|---|
| Dead lift | + | 1" | 29" | 50 | 50 |
| Curl | + | 34" | 63" | 20 | 30 |
| Military | + | 58" | 82" | 40 | 40 |
| Return | − | 80" | 0" | 10 | 10 |

Modeling Sporting Activities

When a weight is lifted the force felt by the lifter is given by the equation $$F = Mg + M\frac{d^2x}{dt^2}$$

Here M is the mass of the weight, g is the acceleration of gravity and the second term is the acceleration of the weight. When starting to lift the weight from its stationary position, the applied force is larger, and once moving the weight can "coast" to its final position with less applied force. This behavior is absent in spring, friction and pneumatic exercise equipment. It can be important in some weight lifting exercises (like the clean and jerk) when the initial acceleration is produced with the stronger muscles of the legs. By monitoring the position of the movable attachment, the velocity and acceleration can be calculated using finite differences and the force applied by the FGU adjusted to approximate this behavior.

In rowing, the apparent force depends on the boat velocity (Vb) and the speed at which the oars are pulled (V). The water exerts drag on the boat proportional to the boat velocity (Vb). This can be modeled by the difference equations:

If $(V>Vb)$ $F=A(V-Vb); Vb=Vpb+dt(F-B\ Vb)/M$

Else $F=C;\ Vb=Vbp-dt(B\ Vb)/M$

Here F is the force on the cable, Vbp is the boat velocity at the last time step, dt is the time step, V is the oar (or cable pulling velocity), M is the mass of the boat and parameters A,B,C are constants selected to model the rowing. This set of equations is constructed in software within the FGU and used in real time to set the applied force F on the cable to simulate rowing.

Software

The software package which runs on a smart phone or other computer organizes the training program as follows 1. User information (height, weight, age, development goals)
2. A plurality of workouts. Examples "Chest", "Upper Body", "Endurance", "Monday's workout".
   Each workout consists of a plurality of exercises which are selected from a master list. The software may order these with various goals like developing a specific muscle group or maintaining the charge on the battery (some exercises tend to deplete the battery, others to charge it).
3. The exercise, which consists of a plurality of "sets".
4. The set which consists of a plurality of repetitions
5. The repetition which is a plurality of movements for the FGU as described above.

The software would set "typical" values for the number of repetitions and sets. The software would set values for the start and stop distances for the movements based on the user's height and the exercise performed. There would also be a library of predefined workouts and predefined set groups like "pyramid", "inverted pyramid" etc. All of the above could be overridden by the user.

The software would display diagrams or videos for each exercise showing how to connect the attachments to the FGU. The software could be configured to "talk" or "beep" to give cadence during a set or prompt the user to start the next set after a time interval.

The software running on a smartphone can track the user performance and function as a personal trainer. The date, time, exercises performed, number of repetitions performed, time to complete each repetition, set and exercise, estimated energy (calories) burned, etc., are recorded and could be displayed as charts and graphs.

The "personal trainer" (PT) can use this data to dynamically adjust the workout for best progress (a "progressive program"). For example, during strength training it is desirable to gradually increase the amount of weight lifted (the resistance) slowly over a period of weeks. The PT can perform this function and display progress on a graph. The PT can also take into account the users performance on a given day, so it the user is having a "good day" as indicated by performing the required repetitions more quickly, the PT can increase the weight slightly on those days.

The PT can perform a "spotter" function and reduce the weight slightly if the user is struggling to lift it. The PT can also interface with the "Apple Iphone Health" application. The PT can send the training data to another user, (for example to allow races or contests between users) to his physician or to a human personal trainer. The user can enter information about injuries to body parts and the PT can adjust the workouts to avoid stressing those body parts. If the user, is using a progressive training program and becomes sick, he can reset his "progress" to an earlier date and work back up.

Preferred Embodiment

A plastic covered steel cable 3/32 inch outside diameter with a working strength of 90 lbs (breaking strength 450 lbs) is readily available and works well with a 3" dia spool. A two stage spur gear transmission provides 50:1 reduction from the motor to the spool with low frictional losses.

A "540 size" (1.5" dia and 2" long) "13.5 turn" sensored brushless motor for a RC car has Kv=50 rev/sec, Ki=0.0033 N*M/A. With the gear ratio of 50, and the 3" dia spool, a current of 40 A would produce a force on the cable of 39 lbs. Using 2 NiCad batteries (2.6V total) it can retract the cable at low force at a speed of 1.6 f/sec.

Figure 12:
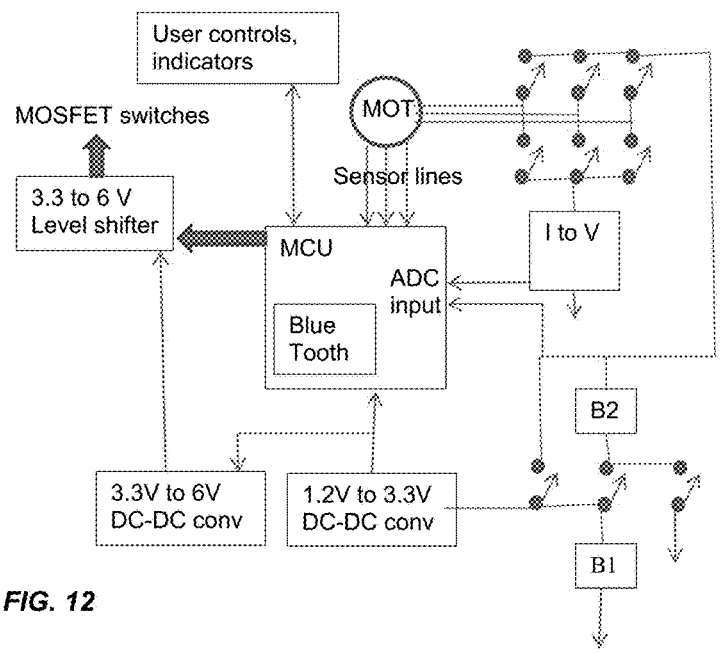
FIG. 12 Circuit block diagram of prototype unit.

The circuit used is shown in FIG. 12. The sensored brushless motor has lower electrical resistance and longer life than brushed motors. In addition, the spool position and velocity can be monitored by counting the commutating pulses. A Hall effect current monitor converts the motor current into a voltage which the microcontroller reads using its ADC. This allows measurement of the motor current and therefore the motor torque. A microcontroller with internal blue tooth, ADC and PWM circuits monitors the motor position and motor current, controls the MOSFET switches and communicates with a smart-phone through blue tooth. DCDC converters and level shift circuits convert the low battery voltage (1.3V) to 3.3V to power the MCU, and to 6V to drive the MOSFET gates. The microcontroller implements negative feed-back from the motor current into PWM signals which drive the motor thereby producing the required programmable torque.

Figure 13:
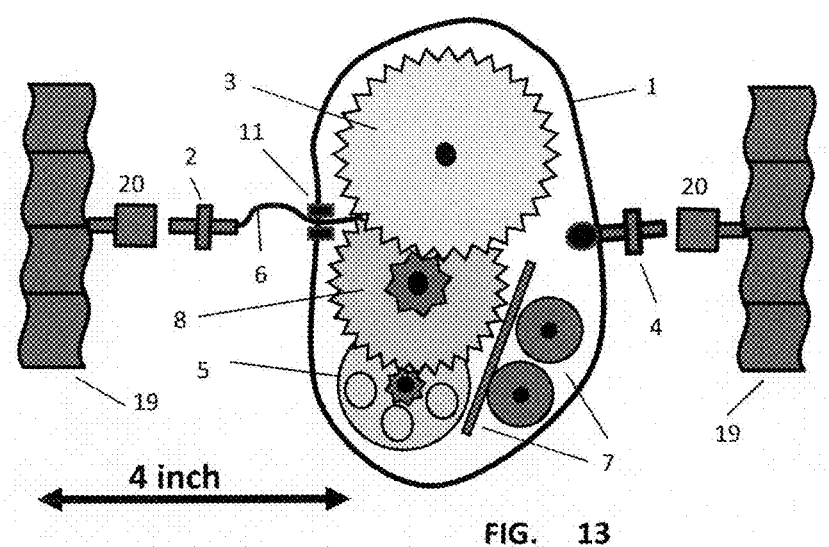
FIG. 13 Disassembled prototype unit.

A photo of a working prototype device is shown in FIG. 13. The entire FGU is 6"×3"×3" and weighs about 1.5 lbs. The QRCs shown are taken from key-chains, but would be replaced with stronger versions.

Prior Art

Elastic cables have been available for years. They are light a compact but many lengths and thicknesses would be required to match the capabilities of this invention, and of course they cannot communicate with a smart phone.

Adjustable dumbbells (where the weight is selected with a rotating dial or pins) are also available, however a heavy 50 lb unit would be required to match the current invention and of course they cannot communicate with a smart phone.

US20140113779 A1 by Andrew Loach, is a small hand held device with extendable cable, transmission, a magnetic or fluid drag resistive element. Also a radio transmitter to some external device for monitoring progress is mentioned. One handle is detachable and one handle is fixed. The spring return and magnetic drag resistance limit the range of force that can be generated, for example a large static force cannot be produced. Setting the start and end points for the exercise is difficult. A two handed exerciser is described but requires a completely different design.

US20090093350 A1, by Henner Jans, presents a small hand held device of similar size to this one. It is purely mechanical with a flywheel and friction mechanism to control the resistance. It does not offer detachable accessories. It would be more difficult to set the length of travel and resisting force. It can not communicate with a smart phone.

U.S. Pat. No. 8,998,779 B1 by Stephen Ihli and Mark Krull is similar to the preceding but has fewer capabilities.

US20110165995 A1 by Paulus, Shaw and Deaconu presents apparatus for computer controlled exercise equipment. The apparatus shares many of the electrical characteristics with the present invention (programmable force generation) but it is not compact, does not offer detachable accessories or multiple exercise types from a single unit or a self-recharging feature.

U.S. Pat. No. 6,511,402 B2 by Shu, Buhler, and Pittaway describes a self powered exercise machine with electrically generated resistance. It is a large single use stair-master machine. It is not useful for strength training. It does not switch rapidly from "motor mode" to "generator mode".

The invention claimed is:
1. An exercise system comprising
   a force generation unit (FGU) small and light enough to be suspended during use comprised of
      housing
      spool attached pivotally to the housing
      electric motor attached to the housing
      transmission attached to the housing linking the motor to the spool electrical system attached to the housing driving the motor plurality of quick release connectors (QRC) attached to the housing cable attached at one end to the spool and the other end to a QRC a set of accessories attachable to the FGU in any combination using the QRCs, consisting of and not limited to:

hand grips, foot loops, leg loops, floor plate, extension cables, temporary or permanent fixed point attachments, extendable rod(s) with pulleys on the end, a sliding seat for rowing with tracks and foot-stop, a soft strap to fit over the shoulder.

2. The system of claim 1 except where the FGU has two spools attached to the housing and driven by the transmission, each spool with its own cable and each cable with its own QRC.

3. The system of claim 1 where the users applied force is used to recharge the internal battery in the FGU during exercise.

4. The system of claim 1 where the FGU monitors the force applied to the movable QRC(s) either through the motor or a separate sensor.

5. The system of claim 4 where the FGU monitors the relative position and/or velocity and/or acceleration of the movable connector(s) either through the motor or separate sensor.

6. The system of claim 2 where batteries are switched between parallel and series configuration during an exercise, to allow the highest rate of battery recharging and the highest operating speed.

7. The system of claim 5 where the FGU has programmable force -vs- position and/or velocity and/or time characteristics.

8. The system of claim 7 where the programmed force creates an approximate model of a sporting activity such as weight lifting or rowing by modeling a differential equation in discretized form.

9. The system of claim 7 where a plurality of force -vs- position and/or velocity characteristics (referred to as "movements") may be grouped together to form an "exercise".

10. The system of claim 9 where a plurality of user customizable exercises (a "workout") are stored in the FGU or on and external and are easily selectable.

11. The system of claim 10 where the FGU can be programmed via a computer, smart-phone or other electronic device.

12. The system of claim 11 where the FGU sends data back to the computer, smart-phone or other electronic device so that the user may track, record or share his performance.

13. The system of claim 12 where the software modifies the parameters of the exercises in the workout program over a period of minutes to weeks to aid the user in his performance goals.

14. The system of claim 1 but with an external moving pulley with QRC to double the generated force.

15. The system of claim 11 where 2 or more FGUs are used simultaneously to increase the force or complexity of an exercise.

* * * * *